United States Patent [19]

Newkirk

[11] 4,240,434
[45] Dec. 23, 1980

[54] PERITONEO-VENOUS SHUNT

[76] Inventor: John B. Newkirk, Rte. 2, Box 302EE, Evergreen, Colo. 80439

[21] Appl. No.: 949,734

[22] Filed: Oct. 10, 1978

[51] Int. Cl.³ ............................................ A61M 25/00
[52] U.S. Cl. .................................. 128/350 V; 137/242
[58] Field of Search ............... 128/350 R, 350 V, 274; 137/846, 847, 242

[56] References Cited

U.S. PATENT DOCUMENTS

| 657,007 | 8/1900 | Richter | 137/846 X |
| 2,867,213 | 1/1959 | Thomas | 128/350 V |
| 3,020,913 | 2/1962 | Meyer | 128/350 V |
| 3,109,429 | 11/1963 | Schwartz | 128/350 V |
| 3,233,610 | 2/1966 | Wade | 128/350 V |
| 3,566,875 | 3/1971 | Stoehr | 128/350 V |
| 3,885,561 | 5/1975 | Cami | 128/350 V X |
| 3,910,283 | 10/1975 | LeVeen | 128/350 V |

FOREIGN PATENT DOCUMENTS

| 301718 | 8/1922 | Fed. Rep. of Germany | 137/846 |
| 914943 | 1/1963 | United Kingdom | 137/846 |

Primary Examiner—Dalton L. Truluck
Attorney, Agent, or Firm—Richard D. Law

[57] ABSTRACT

A peritoneo-venous shunt for the surgical management of ascites includes a perforated inlet catheter with an asymetrical, one-way valve attached to and contained within a pump body, a venous catheter and a plurality of x-ray absorbing markers placed along the catheters for ascertaining their positioning in a patient.

5 Claims, 7 Drawing Figures

PERITONEO-VENOUS SHUNT

The controlling of ascites of diverse etiology in some patients has been accomplished by the use of a shunt which carries ascites liquid from the peritoneal cavity to a vein. This type of treatment was pioneered by a Dr. A. N. Smith, Preshaw, R. M. & Bisset, W. H., "The Drainage of Resistent Ascites by a Modification of the Spitz-Holter Valve Technique", J. Roy. Col. Surg. Edenb., 7:289, 1962, and has since been used in numerous cases of ascites which do not respond to treatment by diuretic medicament such as aldosterone antagonists, steroids, etc. Early attempts included the withdrawal of ascites and the subsequent intravenous transfusion of the same fluid. Since these techniques are hazardous and awkward, several internal shunting techniques have been tested. The JAMA, July 1967, Vol. 201, No. 4, page 118 describes one type of shunt using a standard valve. LeVeen et al describes Shunting of Ascites in Ann. Surg. Oct. 1974, Vol. 180, No. 4, page 580 using a valve in the shunt which had been available for the surgical management of hydrocephalus. In a follow up article, LeVeen et al described a slightly modified form of an ascites shunt in Ann. Surg. November, 1976, Vol. 184, No. 5 page 574. Thus shunt valve, like its predecessor uses silicone rubber struts attached to an outer ring and inwardly to the valve seat for controlling the opening and closing of the valve by pressure.

THE PRESENT INVENTION

The shunt comprising the present invention consists of a proximal or peritoneal catheter, flexible pump body containing a miter valve and a distal catheter. A major part of the system is the duck-bill or miter valve which is placed at the entry end of the pump body. The entry end of the shunt system is a simple collection tube with numerous staggered holes placed along approximately the first half of its length. The entry end of this catheter is cut off at an angle of 45 degrees to provide a short but soft and flexible tip for easy insertion through a nick incision in the peritoneal wall. The downstream end of the peritoneal catheter passes into the proximal end of the shunt pump body where the two components are cemented together. The pump body consists of a roughly cylindrical tube made of biocompatible flexible material. This component is flexible enough to yield to the curvature of its placement site (for examples, rib, iliac crest, pubis), yet rigid enough to return to its cylindrical form when it is pumped by digital squeezing. The tube is cemented along its entire length to a flexible base consisting of silicone rubber, internally reinforced with dacron mesh. This base allows the pump body to be sutured to the placement site tissue at the time of surgery. The miter valve, so termed because of its resemblance to the liturgical head-dress of that name, is located inside the pump body at the extreme distal end of the peritoneal catheter. It is designed and constructed to open at a positive pressure of about one centimeter head of water. When the pressure is reversed no detectable reflux occurs except for about 0.05 ml due to the elastic closure of the valve flaps. Due to its unique asymmetrical construction the opposing flaps of the miter valve slide laterally against one another whenever the pump body is squeezed. This rubbing action tends to dislodge any minute particles which might form on the inside of the valve flaps. Unless they are continually removed from these critical surfaces such deposits might in time build up enough to render the valve incompetent. The distal catheter is a biocompatible flexible tube that contains no fenestration holes. It is permanently cemented to the pump body. Its open exit end is cut off at a 45° angle to facilitate its entry into a vein via a small venotomy and to assist its passage through the vein. Unless the pump body is deliberately pumped, as by squeezing it between the fingers, liquid will flow uniformly through the system under the influence of a constant positive hydraulic pressure. However, when the pump body is sharply squeezed, the liquid will be forced rapidly through the distal catheter. This manipulation allows the surgeon, attendant or even the patient himself to clear the distal catheter of any solid matter that may be accumulating there. A plurality of tantalum or other x-ray absorbing markers may be placed on the catheters and on the pump body to assist in their placement at operation.

OBJECTS AND ADVANTAGES OF THE INVENTION

Included among the objects and advantages of the invention is to provide an improved ascites shunt.

Another object of the invention is to provide an ascites shunt with a self cleaning valve.

Still another object of the invention is to provide a self cleaning valve.

Yet another object of the invention is to provide an asymetric miter valve which tends to scour and clean its opening on any increase in back pressure on the discharge end of the valve.

An additional object of the invention is to provide an ascites shunt having a plurality of radio-opaque markers for ascertaining the positioning of certain parts of the shunt.

A further object of the invention is to provide an ascites shunt which is complete and ready for sterilization before implanting into a patient and is provided with anchoring means for the manual manipulative portions of the shunt.

These and other objects and advantages of the invention may be ascertained by reference to the following description and appended illustrations.

GENERAL DESCRIPTION OF THE DRAWINGS

SPECIFIC DESCRIPTION OF THE DRAWINGS

Figure 1:
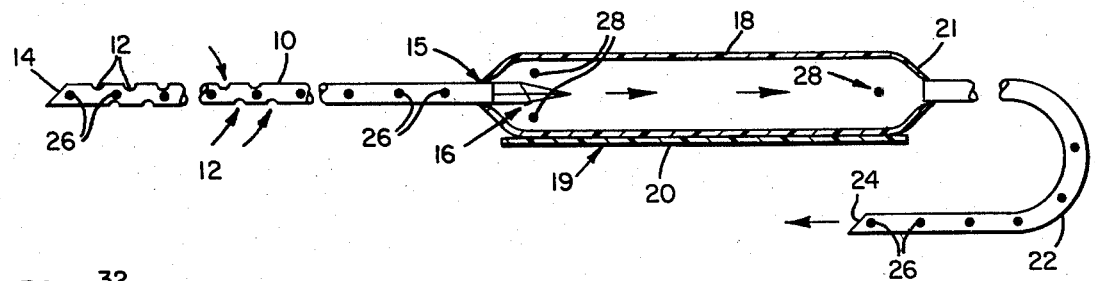
FIG. 1 is a side elevational view, partly cut away, of an ascites shunt according to the invention.

The unit selected for illustration in FIG. 1, includes a soft, flexible (intake) catheter 10, formed of medical grade silicone rubber, having a plurality of inlet openings 12 along part of its length and an angle cut end 14. The catheter is tubular and about 20 cm long including a non-perforated section about 10 cm long. A one way asymetrical miter valve 16 is mounted on end 15 of the non-perforated section of the catheter. A pump section 18 is secured, as by cementing, at end 19 to the non-perforated section of tubing with the valve 16 enclosed inside the tubular pump 18. This pump is also made of medical grade silicone rubber, and is about 1.3 cm O.D. and 5 to 7 cm long. A fixation base 20, of silicone rubber, is secured to the pump 18 to permit the pump to be anchored, as by suturing, in a preselected position in a patient. Pump end 21 converges to soft, resilient tubing 22 which is the distal (venous) catheter of the unit, terminating in a 45° angle cut 24. This catheter may have a length of some 70 cm. A plurality of x-ray absorbing markers 26 are applied to the catheters to ascertain the implanted positions of the catheters. These markers must be medically acceptable, and may be placed every few centimeters along the catheter tubing. Larger markers 28 may be placed on the pump body 18 to ascertain its position in a patient. These markers may contain tantalum or other acceptable material embedded or otherwise applied to the silicone rubber. The pattern of the markers may be arranged so that the exact location of the members is readily detected by x-rays.

The valve for the shunt may have several forms, being variations of an asymetrical configuration. The asymetry causes differential movement of the leaf or flap portions of the valve, giving a sliding, translational motion to the opposing surfaces. This sliding motion tends to keep the adjacent valve surfaces free of particulate matter that otherwise might accumulate.

Figure 2:
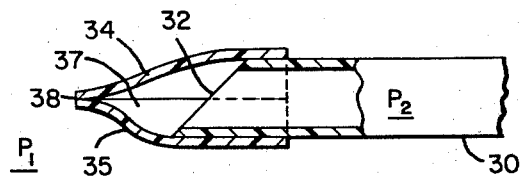
FIG. 2 is a sectional side elevational view of one form of an asymmetrical miter valve, according to the invention, mounted on an end of a catheter.
Figure 3:
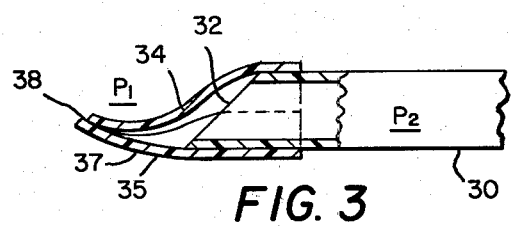
FIG. 3 is a sectional, side elevational view of the form shown in FIG. 2 but in the configuration taken when $P_1$ is greater than $P_2$.

The variation shown in FIGS. 2 and 3 include a semi-rigid tube 30, made of resiliant biocompatible material such as medical grade silicone rubber, which has an end 32 cut at an angle of approximately 45° to the transverse plane which is normal to the tube axis. The valve itself is formed of soft, elastic, flexible, biocompatible material such as low durometer silicone rubber sheets consisting of two halves 34 and 35. In its present form these halves are cemented together along the juxtaposed edges 36 and 37 of the sheets, forming joining lines 36 and 37 on opposite sides of the valve thereby forming a thin-walled tube at one end when the sheets are stretched over tube 30. The tubular end is then sealed onto the end of the catheter 30 and the other end is allowed to remain in the flat configuration where opposite sides of the tube wall are flat and closed, but not sealed together at the end, leaving a slit opening 38. The length of slit has a relation, along with the wall thickness, rubber durometer, etc. in determining the necessary pressure differential for opening and closing the valve.

Figure 7:
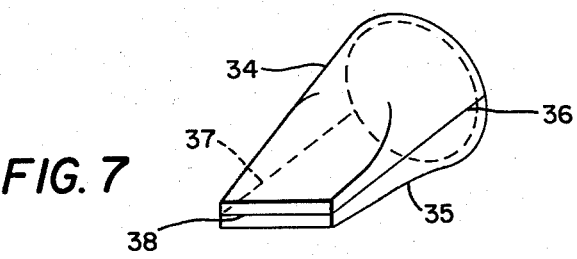
FIG. 7 is a perspective view of the assembled and formed valve, ready to be placed over the end of tube 30, 40, or 50.

The action of the valve of FIGS. 2 and 7 on the slant end catheter is shown in FIG. 3 when the pressure $P_1$, externally of the valve, increases above the internal tubular pressure $P_2$. The sides of the asymetrical slit valve are depressed unequally, e.g., according to the surface area of the halves available for the depression. Thus, the upper half 34 has a larger area (above the slanted end) as opposed by the smaller area of lower half 35 under the slanted end) in FIGS. 2 and 7. The greater total pressure causes the top to depress more than the bottom resulting in a differential movement of the lips of slit and, also, causing the lips to press tighter together, preventing back flow into the catheter 30. An increase of pressure $P_2$ above the pressure $P_1$ causes a flow of fluid through the valve and out of the catheter. The translational relative movement of the lips against one another tends to scour the internal surfaces of the lips thereby tending to remove any thicking material which may be there.

Figure 4:
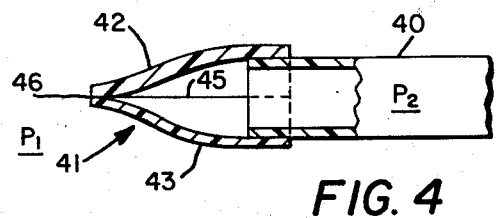
FIG. 4 is a sectional, side elevational view of a further modified asymmetrical valve of the invention.

The asymetrical valve of FIG. 4 includes a catheter end 40 and a miter valve, shown generally by numeral 41. The valve includes an upper half 42 and a lower half 43 joined on side joints 45 (one on each side) leaving an open slit 46. The wall of the upper half 42 is thicker than the wall of the lower half 43, causing the thinner (weaker) wall to be depressed more when the external pressure $P_1$ around the valve exceeds the internal pressure $P_2$ in the valve and the catheter 40. When there is a greater fluid pressure from inside, the valve 41 opens (normally the bottom lip moves more) to release fluid from inside the catheter 40 through the valve 41. The depressing action of the greater external pressure causes a sliding motion of the lips of the valve for the cleansing action previously described.

Figure 5:
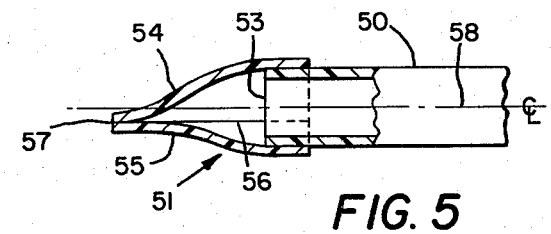
FIG. 5 is a sectional, side elevational view of still another form of the invention.
Figure 6:
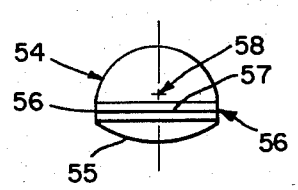
FIG. 6 is an end elevational view of the device of FIG. 5.

The modifications of FIGS. 5-6 include a catheter 50 with a slit valve shown generally by numeral 51. The catheter has a square cut end 53, with the valve covering the square cut end. The valve is formed of two portions, an upper portion 54 and a lower portion 55, joined on opposed joint lines 56, only one being shown. The upper portion covers more than ½ a split tube so there is more surface area on the upper portion (above the joint lines) than on the lower portion. The valve is provided with a slit 57. The portions may be arranged so that when sealed along their sides 56 and formed into the closed slit configurations, the slit does not contain the axis 58 of the catheter 50. The detailed geometry of this off-axis principle may be varied, depending on the dimensional parameters assigned on and the desired pressure-flow characteristics of the valve.

An example of the use of the present device is for the surgical management of ascites. In this case the shunt is totally implanted in the patient with the proximal catheter in the peritoneal cavity for collection of ascites liquid. The pump portion 18 is sutured into place (sometimes on or adjacent to the lower rib cage) for protection and yet is accessible for percutaneous pumping. The distal catheter is tunneled subcutaneously to where the venous end may be inserted into a vein, for example the saphenous or the internal jugular veins. After implanting, the position of the implanted unit may then be ascertained by x-ray absorbing markers. The unit is checked for good working order, after which the wounds are closed according to accepted medical procedures. The pump may be actuated periodically (by squeezing the pump body percutaneously) to clean the valve, to flush the distal tubing and to confirm shunt patency. The x-ray absorbing markers permit periodic confirmation of position of the shunt components without injecting contrast medium into the shunt system.

What is claimed is:

1. An ascites shunt for completely implanting in a patient comprising:
   (a) a flexible semi-rigid medically acceptable catheter for implanting in the peritoneal cavity of a patient, said catheter having an open end cut at an acute angle and a substantial portion of said catheter adjacent said open end being perforated to facilitate entry of liquid into the shunt system:
   (b) a pump body secured to and in communication with the distal end of said catheter opposite said perforated end, consisting of an enlarged, flexible, roughly tubular member of medically acceptable material;

(c) an asymetrical, one way miter valve formed as a normally closed tubular slit valve having a flatten end at the slit with a top portion and a bottom portion for one way fluid flow through the slit and constructed and arranged so that one of the top and the bottom portions moves more than the other on closing to cause a rubbing action of the top portion on the bottom portion, mounted on the end of said perforated catheter inside said pump body permitting pumping of said pump body with no reverse flow; and (d) a second catheter secured to the outlet of said pump body, said second catheter being flexible and having its end cut off at an acute angle with a single end outlet, a plurality of absorbing markers secured in the material of the catheters and pump for ascertaining positioning of the parts by x-radiography.

2. An ascites shunt according to claim 1, wherein said valve includes a flexible tube with a flattened and an unsealed end and sides forming said slit, with one side of the flattened end having more area for flexing whereby superior pressure on the outside thereof causes differential movement of the flattened parts of the valve.

3. An ascites shunt according to claim 1, being further characterized by fixation means secured to said pump for securing the same in position in a patient by sutures.

4. An ascites shunt according to claim 1, wherein said miter valve includes said top and bottom portions having different areas of depressible material or different mechanical characteristics so that superior external pressure depresses one portion more than the other.

5. An ascites shunt according to claim 1, wherein said miter valve includes said top and bottom portions one of which is of thicker and/or stiffer material than the other portion and is more resistant to flexing by pressure thereby causing a differential movement of the portions due to superior external pressure on the valve.

* * * * *